United States Patent
Inagaki et al.

(10) Patent No.: US 6,352,632 B1
(45) Date of Patent: Mar. 5, 2002

(54) CONNECTOR FOR NOX SENSOR

(75) Inventors: Hiroshi Inagaki; Noriaki Kondo, both of Aichi (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 09/238,932

(22) Filed: Jan. 28, 1999

(30) Foreign Application Priority Data

Jan. 28, 1998 (JP) .......................................... 10-016032

(51) Int. Cl.$^7$ ........................ G01N 27/407; H01R 13/66
(52) U.S. Cl. ........................ 204/425; 204/406; 123/693; 439/620
(58) Field of Search ........................... 439/620; 204/425, 204/426, 427, 428, 406; 123/693, 694, 696

(56) References Cited

U.S. PATENT DOCUMENTS

| | | | |
|---|---|---|---|
| 4,796,587 A | * | 1/1989 | Nakajima et al. ............ 204/406 |
| 4,981,125 A | * | 1/1991 | Kato et al. .................... 204/406 |
| 5,780,710 A | * | 7/1998 | Murase et al. ................ 73/1.06 |

FOREIGN PATENT DOCUMENTS

| | | | |
|---|---|---|---|
| EP | 0678740 A1 | | 4/1995 |
| WO | 95/30146 | * | 11/1995 |

OTHER PUBLICATIONS

Inagaki et al "NOx Meter Utilizing ZrO2 Pumping Cell", SAE Technical Paper No. 980266, pp. 1–6, Feb./1998.*
Society of Automotive Engineers, Inc., copyright 1996, reference No. 960334, "Thick Film ZrO2 NOx Sensor", Nobuhide Kato et al. Month Unavailable.

* cited by examiner

Primary Examiner—Jill Warden
Assistant Examiner—Kaj K. Olsen
(74) Attorney, Agent, or Firm—Sughrue Mion, PLLC

(57) ABSTRACT

A connector 2b for an NOx sensor is connected via a cable C to an end of a sensor body 2a through which a first pump current and a second pump current flow according to the concentration of oxygen and that of NOx, respectively, contained in a gas to be measured. The connector 2b is provided with not only terminals for inputting a signal to and outputting a signal from the sensor body 2a but also a label resistor RL having resistance corresponding to characteristics (relationship between oxygen concentration and first pump current and that between NOx concentration and second pump current) of the sensor body 2a and label signal output terminals T01 and T02 connected to opposite ends of the label resistor RL. On the basis of characteristics of the sensor body 2a, which are identified from the resistance of the label resistor RL which, in turn, is identified via the terminals T01 and T02, the oxygen concentration and the NOx concentration are accurately obtained from detected values of the first and second pump currents. This enables an NOx sensor to always perform accurate measurement irrespective of variations in characteristics among NOx sensors.

15 Claims, 6 Drawing Sheets

FIG. 4   TABLE OF RANKS FOR NOx SENSORS   (RR=30.1 [KΩ])

| RANK | | IP2 GAIN: 0%$O_2$ DATA [PPM/μA] | | | | | |
|---|---|---|---|---|---|---|---|
| UPPER FIELD: RL[KΩ]<br>LOWER FIELD: VR[V] | | 155~159<br>(α=-2) | 160~164<br>(α=-1) | 165~169<br>(α=0) | 170~174<br>(α=1) | 175~179<br>(α=2) | 180~184<br>(α=3) |
| $I_{P1}$<br>[mA] | 6.500~6.749<br>(β=-2) | 1   2.4<br>0.368 | 2   3.3<br>0.494 | 3   4.3<br>0.625 | 4   5.4<br>0.760 | 5   6.3<br>0.865 | 6   7.5<br>0.997 |
| | 6.750~6.999<br>(β=-1) | 7   8.9<br>1.141 | 8   10.0<br>1.247 | 9   11.5<br>1.382 | 10   13.0<br>1.508 | 11   14.3<br>1.610 | 12   16.2<br>1.749 |
| | 7.000~7.249<br>(β=0) | 13   18.2<br>1.884 | 14   20.0<br>1.996 | 15   22.1<br>2.117 | 16   24.9<br>2.264 | 17   27.4<br>2.383 | 18   30.1<br>2.500 |
| | 7.250~7.499<br>(β=1) | 19   33.2<br>2.622 | 20   36.5<br>2.740 | 21   41.2<br>2.889 | 22   45.3<br>3.004 | 23   51.1<br>3.147 | 24   56.2<br>3.256 |
| | 7.500~7.749<br>(β=2) | 25   61.9<br>3.364 | 26   69.8<br>3.493 | 27   80.6<br>3.640 | 28   90.9<br>3.756 | 29   105.0<br>3.886 | 30   121.0<br>4.004 |
| | 7.750~7.999<br>(β=3) | 31   143.0<br>4.131 | 32   169.0<br>4.244 | 33   210.0<br>4.373 | 34   274.0<br>4.505 | 35   374.0<br>4.628 | 36   562.0<br>4.746 |

ATMOSPHERIC DATA

CONNECTOR FOR NOX SENSOR

FIELD OF THE INVENTION

The present invention relates to a connector for an NOx sensor equipped with input and output terminals for inputting a signal to and outputting a signal from an NOx sensor that measures an NOx concentration.

NOx sensors for measuring the concentration of nitrogen oxides (NOx) contained in gas to be measured (hereinafter referred to as a measurement gas) are disclosed in, for example, EP-A1-0678740 and SAE Paper No. 960334, pp. 137–142, 1996. Such a conventional NOx sensor is composed of oxygen-ion conductive solid electrolyte layers that form a first measurement chamber and a second measurement chamber. The first measurement chamber communicates with a measurement gas via a first diffusion-controlling layer, and the second measurement chamber communicates with the first measurement chamber via a second diffusion-controlling layer. A first oxygen-pumping cell and an oxygen-concentration-measuring cell are formed adjacent to the first measurement chamber and are each composed of a solid electrolyte layer sandwiched between porous electrodes. A second oxygen-pumping cell is formed adjacent to the second measurement chamber and is composed of a solid electrolyte layer sandwiched between porous electrodes.

BACKGROUND OF THE INVENTION

In order to obtain the concentration of NOx contained in a measurement gas, such as exhaust from an internal combustion engine, without influence of other gas components (such as oxygen, carbon monoxide, and carbon dioxide) contained in the measurement gas, the above Nox sensor undergoes the following control.

Electrical current (hereinafter referred to as first pump current) is caused to flow to the first oxygen-pumping cell such that an output voltage from the oxygen-concentration-measuring cell attains a predetermined value, thereby controlling the concentration of oxygen contained in the first measurement chamber to a very low level (for example, about 1000 ppm). The measurement gas whose oxygen concentration has been thus controlled to the low level enters the second measurement chamber. A constant voltage is applied to the second oxygen-pumping cell in such a direction that oxygen is pumped out from the second measurement chamber. Then, by virtue of a catalytic function of the porous electrodes of the second oxygen-pumping cell, the second oxygen-pumping cell decomposes NOx contained in the measurement gas into nitrogen and oxygen and pumps out the thus-obtained oxygen from the second measurement chamber. At this time, on the basis of current flowing through the second oxygen-pumping cell, the NOx concentration of the measurement gas is obtained.

The first pump current is controlled such that the concentration of oxygen contained in the first measurement chamber attains low level, but not zero, for the following reason. If the concentration of oxygen contained in the first measurement chamber is controlled to zero, the porous electrodes that constitute the first oxygen-pumping cell cause decomposition of NOx contained in the measurement gas that has entered the first measurement chamber. This disables measurement of NOx concentration through use of the second oxygen-pumping cell.

The above NOx sensor can obtain not only the concentration of NOX contained in the measurement gas from the second pump current but also the concentration of oxygen contained in the measurement gas from the first pump current.

However, a characteristic indicative of the relationship between NOx concentration and second pump current and that between oxygen concentration and first pump current somewhat differ among NOx sensors. If, on the assumption that NOx sensors have certain common characteristics indicative of the relationships, the NOx concentration and the oxygen concentration of a measurement gas are obtained from the second and first pump currents, respectively, detected by the NOx sensor, some NOx sensors may fail to provide sufficiently high measurement accuracy.

An object of the present invention is to provide sufficiently high accuracy in measurement by an NOx sensor regardless of variations in characteristics among NOx sensors.

According to the present invention there is provided a connector for an NOx sensor, which connector comprises input and output terminals for inputting a signal to and outputting a signal from the NOx sensor. The NOx sensor comprises a first measurement chamber and a second measurement chamber. The first measurement chamber comprises a first oxygen-pumping cell and an oxygen-concentration-measuring cell and communicates with a measurement gas via a first diffusion-controlling layer. The first oxygen-pumping cell and the oxygen-concentration-measuring cell are each formed of an oxygen-ion conductive solid electrolyte layer sandwiched between porous electrodes. The second measurement chamber comprises a second oxygen-pumping cell and communicates with the first measurement chamber via a second diffusion-controlling layer. The second oxygen-pumping cell is formed of an oxygen-ion conductive solid electrolyte layer sandwiched between porous electrodes. A first pump current is caused to flow to the first oxygen-pumping cell such that an output voltage from the oxygen-concentration-measuring cell is maintained at a constant value so as to control the concentration of oxygen contained in the first measurement chamber to a constant level. A constant voltage is applied to the second oxygen-pumping cell in such a direction that oxygen is pumped out from the second measurement chamber. There is detected a second pump current that flows through the second oxygen-pumping cell as a result of the application of the constant voltage and according to the concentration of NOx contained in a measurement gas.

The connector for an NOx sensor is equipped with a label resistor having resistance corresponding to at least either a relationship between the concentration of oxygen contained in the measurement gas and the first pump current or a relationship between the concentration of NOx contained in the measurement gas and the second pump current, and is equipped with a pair of label signal output terminals connected to opposite ends of the label resistor.

The thus-configured connector for an NOx sensor is used in the following manner. The resistance of the label resistor is detected via the label signal output terminals to thereby identify characteristics of the NOx sensor concerned. Subsequently, the first pump current is caused to flow to the first oxygen-pumping cell such that an output voltage from the oxygen-concentration-measuring cell becomes constant, i.e., such that the concentration of oxygen contained in the first measurement chamber becomes constant. Also, a constant voltage is applied to the second oxygen-pumping cell in such a direction that oxygen is pumped out from the second measurement chamber. The NOx concentration and the oxygen concentration of the measurement gas are respectively obtained from the second pump current, which flows through the second oxygen-pumping cell according to the concentration of NOx contained in the measurement gas, and the first pump current, which flows according to the concentration of oxygen contained in the measurement gas, as well as on the basis of a characteristic(s) of the NOx sensor identified by the resistance of the label resistor.

SUMMARY OF THE INVENTION

Accordingly, through use of the connector of the present invention for an NOx sensor, a characteristic (at least either relationship between NOx concentration and second pump current or relationship between oxygen concentration and first pump current) of an NOx sensor can be identified by the resistance of the label resistor. Through employment of the identified characteristic(s) of the NOx sensor, the NOx concentration and the oxygen concentration of the measurement gas can be obtained at a sufficiently high degree of accuracy.

Through identification of the relationship between NOx concentration and second pump current, variations in an obtained value of NOx concentration among NOx sensors can be compensated for. Through identification of the relationship between oxygen concentration and first pump current, the concentration of oxygen contained in the measurement gas can be accurately obtained; thus, through compensation of the second pump current on the basis of the thus accurately obtained oxygen concentration, the NOx concentration of the measurement gas can be accurately obtained against variations in the concentration of oxygen contained in the measurement gas.

Further, through identification of both of the above relationships implemented by a minor additional element of a label resistor, the measurement accuracy of the NOx sensor can be significantly improved.

The resistance of the label resistor may correspond to at least the sensitivity of the second pump current to variations in the concentration of NOx contained in the measurement gas.

Problems Solved by the Invention

In the accompanying drawings FIG. 6B schematically shows the relationship between the second pump current and the concentration of NOx contained in the measurement gas. Offset of the second pump current (second pump current at an NOx concentration of 0%) and sensitivity (slope of the graph) differ among NOx sensors.

Through use of a relative value, as opposed to an absolute value, for the second pump current in execution of control, offsets are canceled; thus, through mere compensation for variations in sensitivity, measurement can be performed accurately.

The resistance of the label resistor may correspond to at least the first pump current as measured when the oxygen concentration of the measurement gas is identical to that of the atmosphere.

Again, FIG. 6A schematically shows the relationship between the first pump current and the concentration of oxygen contained in the measurement gas. As shown in FIG. 6A, the first pump current has an offset of 0 and is substantially proportional to the oxygen concentration. Thus, when the first pump current at a certain oxygen concentration is known, the sensitivity of the first pump current to the oxygen concentration can be easily obtained.

Accordingly, from a first pump current as measured when the measurement gas assumes an oxygen concentration identical to that of the atmosphere, the relationship between the first pump current and the concentration of oxygen contained in the measurement gas can be identified. On the basis of the thus-identified characteristic relationship, the concentration of oxygen contained in the measurement gas can be accurately obtained.

Through use of the thus-obtained oxygen concentration, the oxygen concentration dependency of an NOx sensor can be compensated for. Also, the thus-obtained oxygen concentration can be applied to various kinds of control that are performed on the basis of the oxygen concentration of the measurement gas.

The resistance of the label resistor may correspond to not only oxygen concentration but also to air-fuel ratio or excess air factor.

The invention will be further described by way of example with reference to the accompanying drawings, in which:

BRIEF DESCRIPTION OF THE DRAWINGS

FIG. 4 is a table of ranks for NOx sensors;

Figure 1:
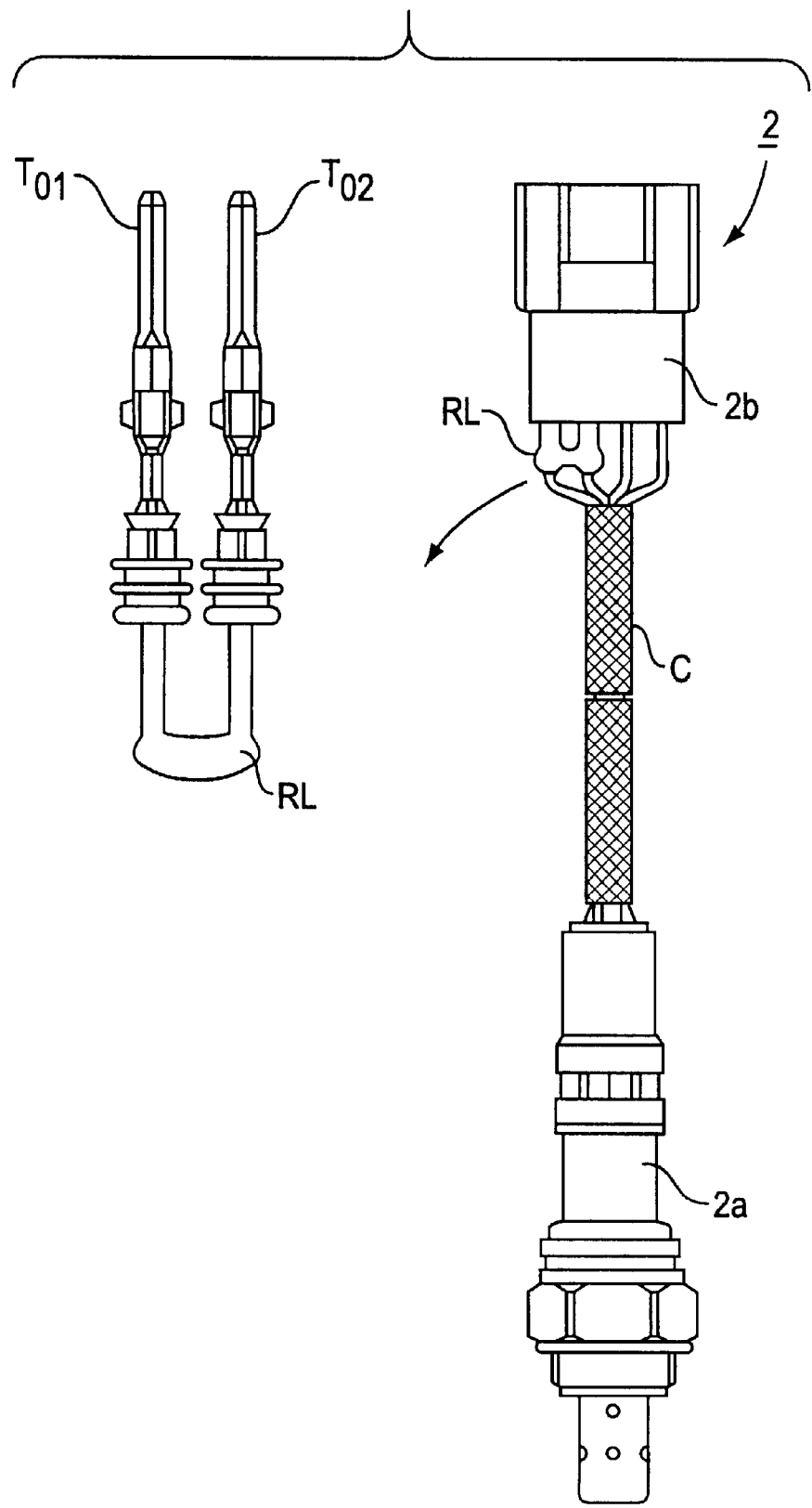
FIG. 1 is a front view showing an NOx sensor equipped with a connector according to an embodiment of the present invention as well as the state of attachment of a label resistor to the connector.

Description of Symbols used in the drawings:
2: NOx sensor equipped with connector
2a: sensor body
2b: connector
4: first pump cell
6: Vs cell
8: second pump cell
12: heater
18, 22, 24: solid electrolyte layer
20: first measurement chamber
26: second measurement chamber
28: spacer
30: NOx concentration detection apparatus
38: label detection circuit
40: drive circuit
42: detection circuit
44: heater electrification circuit
46: temperature sensor
RL: label resistor
RR: reference resistor
T01, T02: label signal output terminal
T11, T12: first pump cell control terminal
T21, T22: Vs cell control terminal T31, T32: second pump cell control terminal T41, T42: heater control terminal

DESCRIPTION OF THE PREFERRED EMBODIMENTS

Figure 2:
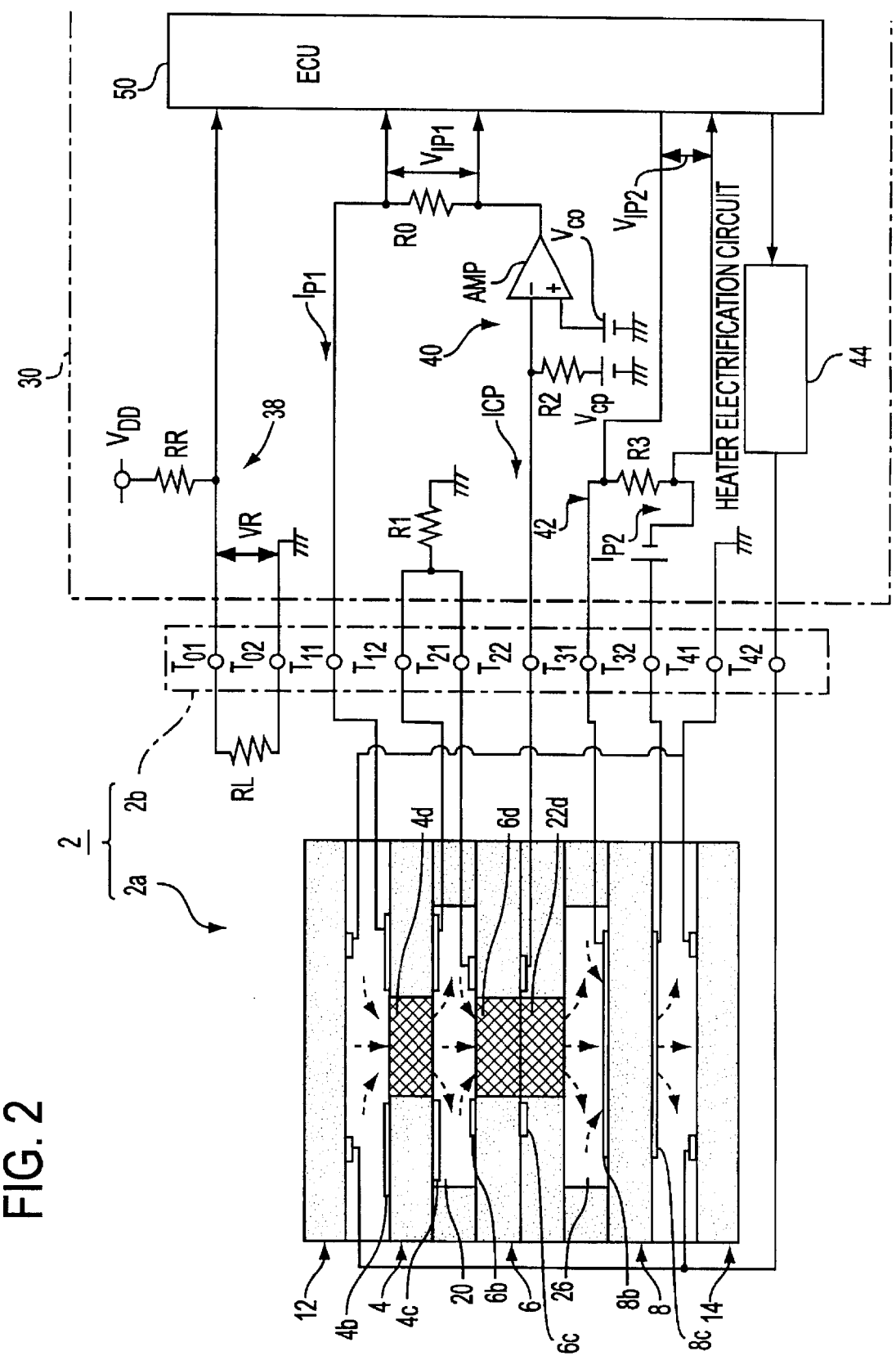
FIG. 2 is a circuit diagram showing the configuration of an NOx concentration detection apparatus which employs an NOx sensor equipped with the connector according to the embodiment.
Figure 3:
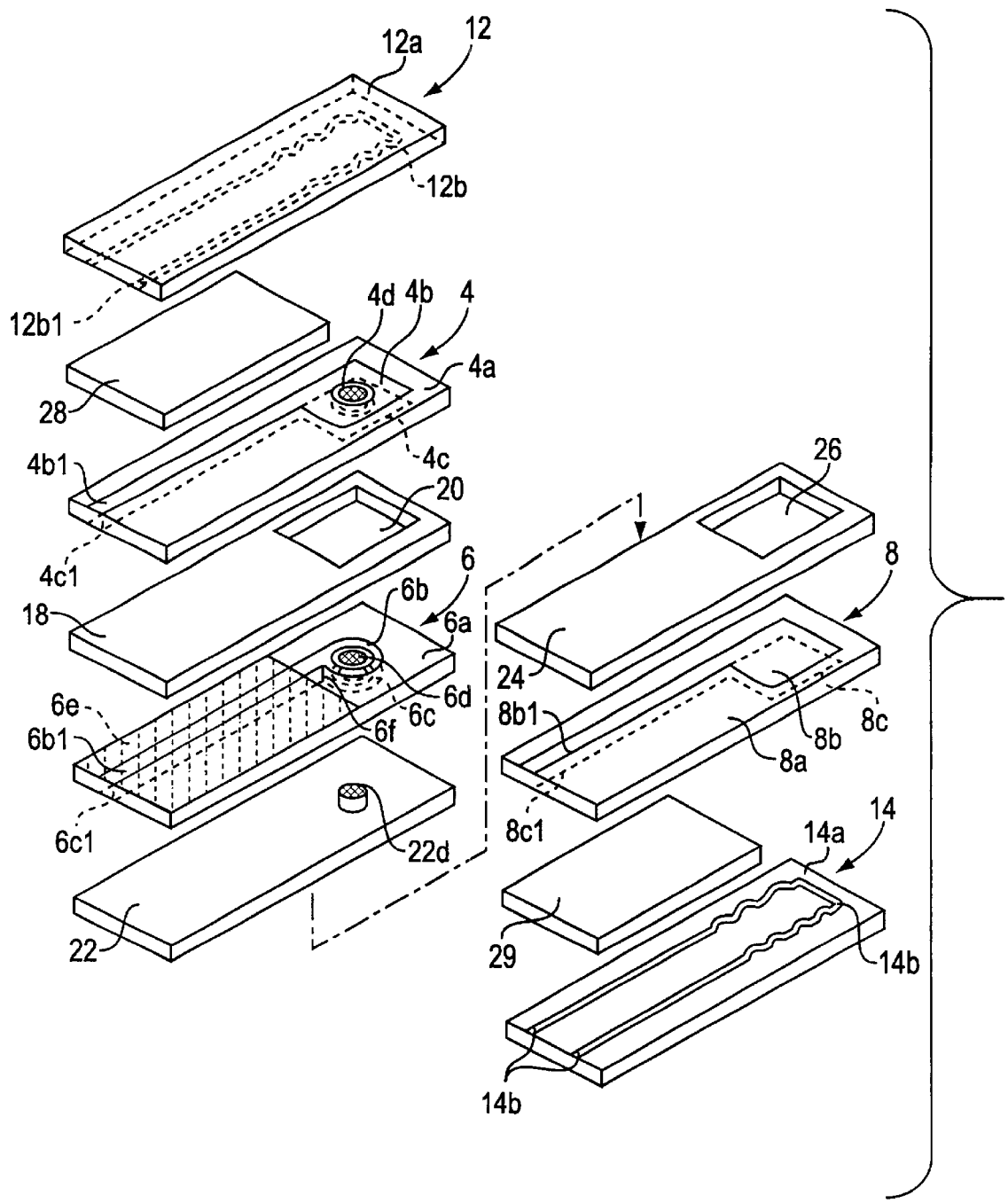
FIG. 3 is an exploded perspective view showing the structure of an NOx sensor body.

FIG. 1 is a front view showing an NOx sensor equipped with a connector according to an embodiment of the present invention. FIG. 2 is a circuit diagram showing the entire configuration of an NOx concentration detection apparatus which employs an NOx sensor equipped with the connector according to the embodiment and which is used for detecting the concentration of NOx contained in exhaust from a vehicle. FIG. 3 is an exploded perspective view of a sensor body.

As shown in FIGS. 1 and 2, an NOx sensor 2 equipped with a connector according to the present embodiment includes a sensor body 2a and a connector 2b connected to an end of the sensor body 2a via a cable C. The sensor body 2a includes a first oxygen-pumping cell (hereinafter referred to as a first pump cell) 4, an oxygen-concentration-measuring cell (hereinafter referred to as a Vs cell) 6, a second oxygen-pumping cell (hereinafter referred to as a second pump cell) 8, and heaters 12 and 14. A first measurement chamber 20 is formed between the first pump cell 4 and the Vs cell 6 and communicates with the exterior of the sensor body 2a via a diffusion-controlling layer 4d. A second measurement chamber 26 is formed between the Vs cell 6 and the second pump cell 8 and communicates with the first measurement chamber 20 via diffusion-controlling layers 6d and 22d.

As shown in FIG. 3, in the sensor body 2a, the first pump cell 4 includes a sheet-like solid electrolyte layer 4a and rectangular porous electrodes 4b and 4c formed on opposite sides of the solid electrolyte layer 4a. Lead portions 4b1 and 4c1 extend from the porous electrodes 4b and 4c, respectively. Further, a round hole is formed in the solid electrolyte layer 4a in such a manner as to penetrate the porous electrodes 4b and 4c at their central portions. The thus-formed round hole is filled with a porous filler to thereby form a diffusion-controlling layer 4d.

The Vs cell 6 includes a sheet-like solid electrolyte layer 6a similar to the solid electrolyte layer 4a of the first pump cell 4 and circular porous electrodes 6b and 6c formed on opposite sides of the solid electrolyte layer 6a. Lead portions 6b1 and 6c1 extend from the porous electrodes 6b and 6c, respectively. Further, a round hole is formed in the solid electrolyte layer 6a in such a manner as to penetrate the porous electrodes 6b and 6c at their central portions. The thus-formed round hole is filled with a porous filler to thereby form a diffusion-controlling layer 6d.

The porous electrodes 4b and 4c of the first pump cell 4 and the porous electrodes 6b and 6c of the Vs cell 6 are located on the solid electrolyte layers 4a and 6a, respectively, such that their centers are aligned with each other. Accordingly, when the first pump cell 4 and the Vs cell 6 are arranged in layers, the diffusion-controlling layers 4d and 6d face each other. The circular porous electrodes 6b and 6c of the Vs cell 6 have a size smaller than that of the rectangular porous electrodes 4b and 4c of the first pump cell 4. An insulation film formed of alumina or a like material is formed on opposite surfaces of the Vs cell 6 so as to cover the lead portions 6b1 and 6c1 from outside in order to prevent current leakage from the lead portions 6b1 and 6c1. Further, a leakage resistance portion 6f is formed between the lead portions 6b1 and 6c1 in order to leak part of oxygen from the porous electrode 6c to the side of the porous electrode 6b through control of current supply, which will be described later.

The first pump cell 4 and the Vs cell 6 are arranged in layers with a solid electrolyte layer 18 interposed therebetween. The solid electrolyte layer 18 has the same shape as that of the solid electrolyte layers 4a and 6a. The solid electrolyte layer 18 has a rectangular hole formed therein in a position corresponding to the porous electrodes 4c and 6b and has a size greater than that of the porous electrode 4c. The thus-formed rectangular hole serves as a first measurement chamber 20.

Also, a solid electrolyte layer 22, which has the same shape as that of the solid electrolyte layers 4a and 6a, is placed on the Vs cell 6 on the side of the porous electrode 6c. The solid electrolyte layer 22 has a round hole formed therein in a position corresponding to the diffusion-controlling layer 6d of the Vs cell 6. The thus-formed round hole is filled with a porous filler to thereby form a diffusion-controlling layer 22d.

As in the case of the first pump cell 4, the second pump cell 8 includes a sheet-like solid electrolyte layer 8a and rectangular porous electrodes 8b and 8c formed on opposite sides of the solid electrolyte layer 8a. Lead portions 8b1 and 8c1 extend from the porous electrodes 8b and 8c, respectively. The second pump cell 8 and the solid electrolyte layer 22 are arranged in layers with a solid electrolyte layer 24 interposed therebetween. The solid electrolyte layer 24 is formed in the same manner as is formed the solid electrolyte layer 18. As a result, a rectangular hole formed in the solid electrolyte layer 24 serves as a second measurement space 26.

Heaters 12 and 14 are placed on the opposite sides of the above-described laminate of the first pump cell 4, the Vs cell 6, and the second pump cell 8, i.e. outside the first pump cell 4 and the second pump cell 8, respectively, such that a predetermined gap is formed between each of the heaters 12 and 14 and the laminate through use of spacers 28 and 29.

The heater 12 (14) includes a heater substrate 12a (14a) having a shape similar to that of the solid electrolyte layers 4a, 6a, and 8a, a heater wiring 12b (14b), and a lead portion 12b1 (14b1) extending from the heater wiring 12b (14b). The heater wiring 12b (14b) and the lead portion 12b1 (14b1) are formed on the side of the heater 12 (14) that faces the first pump cell 4 (second pump cell 8). The spacer 28 (29) is interposed between the heater 12 (14) and the first pump cell 4 (second pump cell 8) and in a position corresponding to the lead portion 12b1 (14b1) so that the heater 12 (14) faces the porous electrode 4b (8c) of the first pump cell 4 (second pump cell 8) with a gap formed therebetween.

The connector 2b has label signal output terminals T01 and T02; first pump cell control terminals T11 and T12 connected to the electrodes 4b and 4c, respectively, of the first pump cell 4; Vs cell control terminals T21 and T22 connected to the electrodes 6b and 6c, respectively, of the Vs cell; second pump cell control terminals T31 and T32 connected to the electrodes 8b and 8c, respectively, of the second pump cell 8; and heater control terminals T41 and T42 for supplying current to the heaters 12 and 14. A label resistor RL is connected to the label signal output terminals T01 and T02. The label resistor RL has a resistance corresponding to a rank indicative of a characteristic of the sensor body 2a.

An NOx concentration detection apparatus 30 determines the concentration of Nox contained in exhaust gas through use of the above-described NOx sensor 2 equipped with the connector and attached to an exhaust pipe of an internal combustion engine carried in a vehicle.

As shown in FIG. 2, the NOx concentration detection apparatus 30 includes a label detection circuit 38 for supplying electricity to the label resistor RL via the terminals T01 and T02 of the connector 2b so as to output a voltage level VR according to the resistance of the label resistor RL; a drive circuit 40 for supplying electricity to the first pump cell 4 and Vs cell 6 of the sensor body 2a via the terminals T11, T12, T21, and T22 of the connector 2b and for detecting first pump current IP1 flowing to the first pump cell 4; a detection circuit 42 for applying a constant voltage to the second pump cell 8 of the sensor body 2a via the terminals T31 and T32 of the connector 2b and for detecting second pump current IP2 which flows through the second pump cell 8 to which the constant voltage is applied; a heater electrification circuit 44 for supplying electricity to the heaters 12 and 14 of the sensor body 2a via the terminals T41 and T42 of the connector 2b so as to heat the cells 4, 6, and 8; and an electronic control unit (hereinafter referred to as ECU) 50, which includes a microcomputer, for controlling the drive circuit 40 and the heater electrification circuit 44 and for determining the NOx concentration and the oxygen concentration of exhaust gas on the basis of detection signals VIP1 and VIP2 issued from the drive circuit 40 and the detection circuit 42, respectively. The porous electrodes 4c and 6b (terminals T12 and T21)—which face the first measurement chamber 20—of the first cell 4 and the Vs cell 6, respectively, are grounded via a resistor R1. The porous electrodes 4b and 6c (terminals T11 and T22) are connected to the drive circuit 40.

The label detection circuit 38 applies a source voltage VDD to an end (terminal T01) of the label resistor RL via a reference resistor RR and grounds the other end (terminal T02) of the label resistor RL. The source voltage VDD is divided by the label resistor RL and the reference resistor RR. A resultant divided voltage is input to the ECU 50 as a voltage level VR.

The drive circuit 40 includes a resistor R2 and a differential amplifier AMP. A constant voltage VCP is applied to an end of the resistor R2, and the other end of the resistor R2 is connected to the porous electrode 6c of the Vs cell 6 (terminal T22). A negative input terminal of the differential amplifier AMP is connected to the porous electrode 6c of the Vs cell 6 (terminal T22); a reference voltage VC0 is applied to a positive input terminal of the AMP; and an output terminal of the AMP is connected to the porous electrode 4b of the first pump cell 4 (terminal T11) via a resistor R0.

The drive circuit 40 operates in the following manner. First, a constant small current iCP is fed to the Vs cell 6 via the resistor R2 to thereby pump out oxygen from the first measurement chamber 20 into the porous electrode 6c. Since the porous electrode 6c is blocked by the solid electrolyte layer 22 and communicates with the porous electrode 6b via the leakage resistance portion 6f, the concentration of oxygen contained in the blocked space of the porous electrode 6c is maintained at a constant level through application of the small current iCP to the Vs cell 6. Thus, the blocked space serves as an internal reference oxygen source.

When the porous electrode 6c of the Vs cell 6 serves as an internal reference oxygen source, an electromotive force is generated in the Vs cell 6 in accordance with the difference in oxygen concentration between the first measurement chamber 20 and the internal reference oxygen source. As a result, a voltage Vs built on the side of the porous electrode 6c (terminal T22) corresponds to the concentration of oxygen contained in the first measurement chamber 20. Since the voltage Vs is applied to the differential amplifier AMP, the differential amplifier AMP outputs a voltage in accordance with the deviation of the input voltage from the reference voltage VC0 (VC0—input voltage). The output voltage is applied to the porous electrode 4b of the first pump cell 4 via the resistor R0.

As a result, the first pump current IP1 flows to the first pump cell 4. Through control of the first pumping current IP1, control is performed such that a constant electromotive force is generated in the Vs cell 6 (between the terminals T21 and T22) (in other words, such that the oxygen concentration of the first measurement chamber 20 becomes constant).

That is, when the measurement gas enters the first measurement chamber 20 via the diffusion-controlling layer 4d, the drive circuit 40 controls the concentration of oxygen contained in the first measurement chamber 20 to a constant level.

The thus-controlled concentration of oxygen contained in the first measurement chamber 20 is set such that a small amount of oxygen (e.g., 1000 ppm) exists, thereby preventing decomposition of NOx contained in the measurement gas contained in the first measurement chamber 20 which would otherwise result from supply of the first pump current IP to the first pump cell 4. The reference voltage VC0 for determining this concentration of oxygen is set to 100 mV to 200 mV. The resistor R0 disposed between the output terminal of the differential amplifier AMP and the porous electrode 4b (terminal T11) is adapted to detect the first pump current IP1. A voltage VIP1 built across the resistor R0 is input to the ECU 50 as a detection signal corresponding to the first pump current IP1.

A constant voltage VP2 is applied between the porous electrodes 8b and 8c of the second pump cell 8 of the sensor body 2a (terminals T31 and T32) via a resistor R3, which is a component of the detection circuit 42. The constant voltage VP2 is applied to the second pump cell 8 in such a direction that the porous electrodes 8c (terminal T32) and 8b (terminal T31) become a positive electrode and a negative electrode, respectively, so that current flows from the porous electrode 8c (terminal T32) to the porous electrode 8b (terminal T31) to thereby pump out oxygen from the second measurement chamber 26. The constant voltage VP2 is set to such a voltage, for example 450 mV, that there can be decomposed NOx contained in the measurement gas which has flowed from the first measurement chamber 20 into the second measurement chamber 26 via the diffusion-controlling layers 6d and 22d, to thereby pump out oxygen generated through the decomposition.

The resistor R3 is adapted to convert to a voltage VIP2 the second pump current IP2 flowing through the second pump cell 8 (between the terminals T31 and T32) as a result of application of the constant voltage VP2 and adapted to input the voltage VIP2 to the ECU 50 as a detection signal corresponding to the second pump current IP2.

In the thus-configured NOx concentration detection apparatus 30, the drive circuit 40 controls to a constant level the concentration of oxygen contained in the measurement gas which has flowed into the first measurement chamber 20 via the diffusion-controlling layer (first diffusion-controlling layer) 4d. The measurement gas controlled to a constant oxygen concentration flows from the first measurement chamber 20 into the second measurement chamber 26 via the diffusion-controlling layers (second diffusion-controlling layers) 6d and 22d. Accordingly, the first pump current IP1 flowing to the first pump cell 4 varies in accordance with the concentration of oxygen contained in the measurement gas. The second pump current IP2 flowing through the second pump cell 8 varies in accordance with the concentration of NOx contained in the measurement gas.

The detection signals VIP1 and VIP2 corresponding to the first and second pumping currents IP1 and IP2, respectively, and the voltage level VR corresponding to the label resistor RL are converted to digital data by an unillustrated A/D converter. Reading and carrying out a predetermined computation on the digital data, the ECU 50 determines the concentration of oxygen and NOx contained in the measurement gas.

In order to secure accuracy of measuring the oxygen and NOx concentrations, the temperature of the sensor body 2a must be controlled to a constant level. To meet this end, the ECU 50 controls current supplied to the heaters 12 and 14 (between terminals T41 and T42) from the heater electrification circuit 44 so that the sensor temperature attains a target value.

FIG. 4 is a table showing the relationship between variations in characteristics of the sensor body 2a and ranks identified by the resistance of the label resistor RL.

As shown in FIG. 4, according to the present embodiment, variations in the first pump current IP1 as measured when the oxygen concentration of the measurement gas is set identical to that of the atmosphere (20.9%) (hereinafter referred to as atmospheric data) are classified into six categories; and variations in gain of the second pump current IP2 as measured while the NOx concentration of the measurement gas is varied with the oxygen concentration of the measurement gas held at 0% (hereinafter referred to as 0% $O_2$ data) are classified into six categories.

Specifically, the atmospheric data are classified into the following six categories (unit: mA): 6.500 to 6.749; 6.750 to 6.999; 7.000 to 7.249; 7.250 to 7.499; 7.500 to 7.749; and 7.750 to 7.999. A correction coefficient $\beta$ is assigned values of −2 to 3 for the respective categories.

The 0% $O_2$ data are classified into the following six categories (unit: ppm/$\mu$A): 155 to 159; 160 to 164; 165 to 169; 170 to 174; 175 to 179; and 180 to 184. A correction coefficient $\alpha$ is assigned values of −2 to 3 for the categories.

Since the atmospheric data are classified into six categories and the 0% $O_2$ data are classified into six categories, a total of 36 categories are established. The 36 categories are respectively named ranks 1 to 36. Each rank is assigned a different combination of values for the correction coefficients $\alpha$ and $\beta$.

In the present embodiment, the reference resistor RR of the label detection circuit 38 has a resistance of 30.1 k$\Omega$; the source voltage VDD is 5 V; and the resistance of the label resistor RL is set as described in the upper field of each cell of the table of FIG. 4 so that the voltage level VR differs by not less than 100 mV between ranks 1 to 36. The lower field of each cell carries the voltage level VR to be input to the ECU 50 when the resistance of the label resistor RL is set as described in the upper field.

In each of ranks 1 to 36, the center value of the corresponding atmospheric data and the center value of the corresponding 0% $O_2$ data are standard values Ast($\beta$) and GP2st($\alpha$), respectively, representative of the rank.

Specifically, in ranks 1 to 6 to which a correction coefficient $\beta$ of −2 is assigned, Ast($\beta$) is 6.625 mA; in ranks 7 to 12 to which a correction coefficient $\beta$ of −1 is assigned, Ast($\beta$) is 6.875 mA; in ranks 13 to 18 to which a correction coefficient $\beta$ of 0 is assigned, Ast($\beta$) is 7.125 mA; in ranks 19 to 24 to which a correction coefficient $\beta$ of 1 is assigned, Ast($\beta$) is 7.350 mA; in ranks 25 to 30 to which a correction coefficient $\beta$ of 2 is assigned, Ast($\beta$) is 7.625 mA; and in ranks 31 to 36 to which a correction coefficient $\beta$ of 3 is assigned, Ast($\beta$) is 7.875 mA.

In rank (6n+1) (where n=0, 1, . . . , 5) to which a correction coefficient $\alpha$ of −2 is assigned, GP2st($\alpha$) is 157 ppm/$\mu$A; in rank (6n+2) to which a correction coefficient $\alpha$ of −1 is assigned, GP2st($\alpha$) is 162 ppm/$\mu$A; in rank (6n+3) to which a correction coefficient $\alpha$ of 0 is assigned, GP2st($\alpha$) is 167 ppm/$\mu$A; in rank (6n+4) to which a correction coefficient $\alpha$ of 1 is assigned, GP2st($\alpha$) is 172 ppm/$\mu$A; in rank (6n+5) to which a correction coefficient $\alpha$ of 2 is assigned, GP2st($\alpha$) is 177 ppm/$\mu$A; and in rank (6n +6) to which a correction coefficient $\alpha$ of 3 is assigned, GP2st($\alpha$) is 182 ppm/$\mu$A.

Since the categories of the atmospheric data are identical in data span, the standard value Ast($\beta$) of the atmospheric data for a rank whose correction coefficient is $\beta$ is calculated by Expression (1) below through use of the correction coefficient $\beta$ and the standard value Ast(0) (=7.125 mA; standard value Ast($\beta$) at a correction coefficient $\beta$ of 0).

$$\text{Ast}(\beta)=\text{Ast}(0)+0.250\times\beta(\text{mA}) \quad (1)$$

Figure 6A:
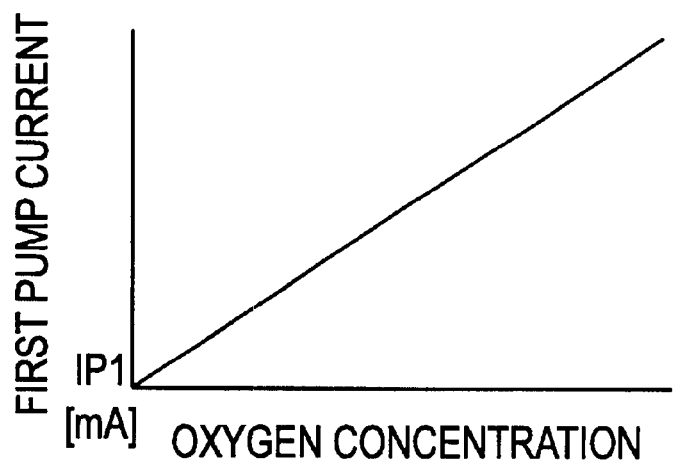
FIGS. 6A and 6B show graphs schematically showing the relationship between oxygen concentration and first pump current and that between NOx concentration and second pump current.
Figure 6B:
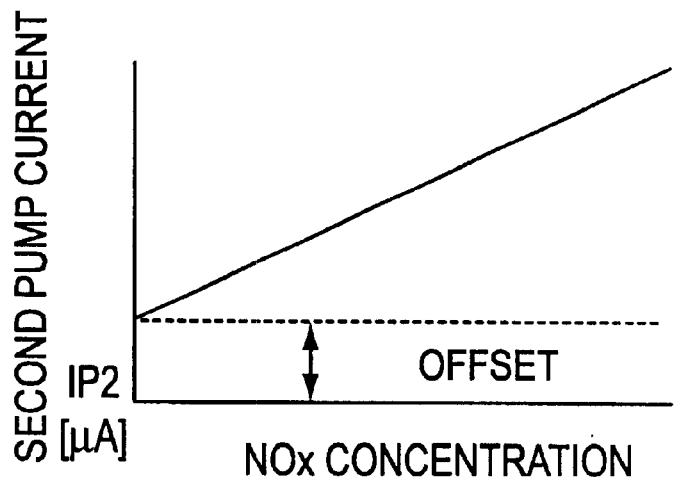

As shown in FIG. 6, the first pump current IP1 and the oxygen concentration are directly proportional. Thus, in the case of the correction coefficient $\beta$, the standard gain GP1st ($\beta$) in the first pump current IP1 with respect to the oxygen concentration can be calculated by Expression (2) below through use of the standard value Ast($\beta$) and the fact that the oxygen concentration of the atmosphere is 20.9%.

$$\text{GP1st}(\beta)=20.9/\text{Ast}(\beta) \ (\%/\text{mA}) \quad (2)$$

$$=20.9/(\text{Ast}(0)+0.250\times\beta) \quad (2a)$$

Since the categories of the 0% $O_2$ data are also identical in data span, the standard value (standard gain) GP2st($\alpha$) of the 0% $O_2$ data for a rank whose correction coefficient is $\alpha$ is calculated by Expression (3) below through use of the correction coefficient $\alpha$ and the standard value GP2st(0) (=167 ppm/$\mu$A; standard value GP2st($\alpha$) at a correction coefficient $\alpha$ of 0).

$$\text{GP2st}(\alpha)=\text{GP2st}(0)+5\times(\text{ppm}/\mu\text{A}) \quad (3)$$

Through use of the thus-calculated standard gains GP1st ($\beta$) and GP2st($\alpha$) and Expressions (4) and (5) below, the oxygen concentration and the NOx concentration of the measurement gas can be obtained from a detected value of the first pump current IP1 and a detected value of the second pump current IP2, respectively.

$$\text{Oxygen concentration}=\text{IP1}\times\text{GP1st}(\beta) \quad (4)$$

$$\text{NOx concentration}=\text{IP2}\times\text{GP2st}(\alpha)+\text{IP2off} \quad (5)$$

where IP2off is the offset of the second pump current that flows at an NOx concentration of 0%.

Figure 5:
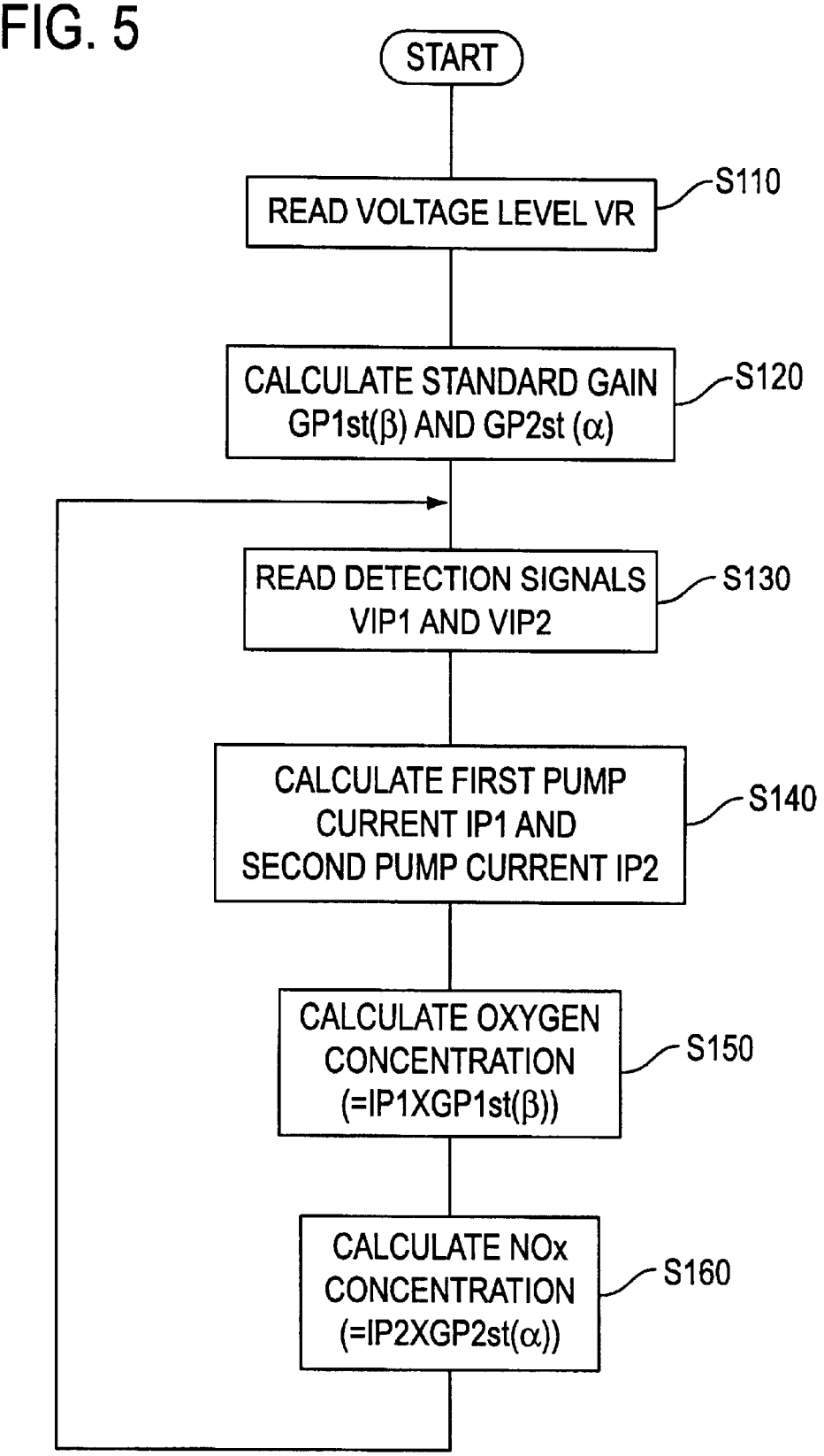
FIG. 5 is a flowchart showing processing to be executed by ECU of the NOx concentration detection apparatus.

When the resistance of the label resistor RL is set as described above, the ECU 50 executes processing as represented by the flowchart of FIG. 5 in order to measure the oxygen concentration and the NOx concentration of the measurement gas.

In step S110, the ECU 50 reads the voltage level VR output from the label detection circuit 38. Subsequently, in step S120, on the basis of values of the correction coefficients $\alpha$ and $\beta$ for the rank 1–36 corresponding to the read voltage level VR, the ECU 50 calculates the standard gain GP1st($\beta$) for the first pump current IP1 with respect to the oxygen concentration and the standard gain GP2st($\alpha$) for the second pump current IP2 with respect to the NOx concentration in accordance with the above Expressions (2a) and (3), respectively.

In step S130, the ECU 50 reads the detection signals VIP1 and VIP2. In step S140, the ECU 50 calculates the first pump current IP1 (=VIP1/R0) and the second pump current IP2 (=VIP2/R1).

In step S150, on the basis of the standard gain GP1st($\beta$) calculated in step S120 and the first pump current IP1 calculated in step S140, the ECU 50 calculates the oxygen concentration in accordance with Expression (4). In step S160, on the basis of the standard gain GP2st($\alpha$) calculated in step S120 and the second pump current IP2 calculated in step S140, the ECU 50 calculates the NOx concentration in accordance with Expression (5). Then, the ECU 50 returns to step S130 and repeats steps S130 through S160.

Herein, the NOx concentration and the oxygen concentration are simply measured. However, since the relationship between the NOx concentration and the second pump current IP2 depends on the oxygen concentration, the NOx concentration obtained in step S160 may be corrected for the oxygen concentration obtained in step S150.

As described above, according to the present embodiment, in the NOx sensor 2 equipped with the connector, the label resistor RL whose resistance corresponds to rank assigned to the sensor body 2a is attached to the connector 2b.

Thus, according to the present embodiment, through identification of the resistance of the resistor RL, a characteristic of the sensor body 2a can be identified. On the basis of the identified characteristic of the sensor body 2a, the NOx concentration and the oxygen concentration of the measurement gas can be accurately measured.

Also, according to the present embodiment, both relationships between NOx concentration and second pump current and between oxygen concentration and first pump current serve as characteristics of the sensor body 2a and are made to correspond to the resistance of a single label resistor RL.

Specifically, two different characteristics of the sensor body 2a can be identified simply by adding a single resistor and two terminals for identifying the resistance of the resistor to the connector 2b. Thus, through employment of minimal configuration, detection accuracy can be significantly improved.

Further, according to the present embodiment, the ranks have identical spans of atmospheric data and 0% $O_2$ data, so that the standard values (standard gains) Ast($\beta$) and GP2st ($\alpha$) that represent the atmospheric data and the 0% $O_2$ data, respectively, in each rank, can be calculated through use of simple expressions that employ the correction coefficients $\beta$ and $\alpha$ and Ast(0) and GP2st(0), respectively.

Thus, according to the present embodiment, in the NOx concentration detection apparatus 30, there is no need for storing the standard values Ast($\beta$) and GP2st($\alpha$) for every rank; accordingly, the required storage capacity can be reduced.

While the embodiment of the present invention, as herein disclosed, constitutes a preferred form, it is to be understood that other forms might be adopted.

For example, in the above-described embodiment, the standard values Ast($\beta$) and GP2st($\alpha$) are calculated through use of $\alpha$ and $\beta$. However, if a sufficiently large storage capacity is available, a table that contains all standard values may be prepared, so that relevant standard values may be read through input of the correction coefficients $\alpha$ and $\beta$.

The above-described embodiment employs 36 ranks because the voltage level VR differs by at least 100 mV between ranks so that the ECU 50 can reliably identify the voltage level VR. However, the number of ranks may be increased so long as the ECU 50 can reliably identify the voltage level VR.

While the invention has been described in detail and with reference to specific embodiments thereof, it will be apparent to one skilled in the art that various changes and modifications can be made therein without departing from the spirit and scope thereof.

What is claimed is:

1. A connector for an NOx sensor, said NOx sensor detecting the concentration of oxygen and NOx contained in a measurement gas, said connector being connected to the NOx sensor and having input and output terminals for inputting and outputting signals to and from the NOx sensor, wherein the NOx sensor comprises a first measurement chamber having a first oxygen-pumping cell and an oxygen-concentration-measuring cell and communicating with measurement gas via a first diffusion-controlling layer, the first oxygen-pumping cell and the oxygen-concentration-measuring cell being each formed of an oxygen-ion conductive solid electrolyte layer sandwiched between porous electrodes; and a second measurement chamber having a second oxygen-pumping cell and communicating with the first measurement chamber via a second diffusion-controlling layer, the second oxygen-pumping cell being formed of an oxygen-ion conductive solid electrolyte layer sandwiched between porous electrodes, and wherein a first pump current is caused to flow to the first oxygen-pumping cell such that an output voltage from the oxygen-concentration-measuring cell is maintained at a constant value so as to control the concentration of oxygen contained in the first measurement chamber to a constant level; a constant voltage is applied to the second oxygen-pumping cell in such a direction that oxygen is pumped out from the second measurement chamber; and a second pump current that flows through the second oxygen-pumping cell as a result of the application of the constant voltage and according to the concentration of NOx contained in the measurement gas is detected, said connector for the NOx sensor further comprising:
a single label resistor having a resistance corresponding to both a relationship between the concentration of oxygen contained in the measurement gas and the first pump current and a relationship between the concentration of NOx contained in the measurement gas and the second pump current; and
a pair of label signal output terminals connected to opposite ends of said label resistor.

2. A connector for an NOx sensor according to claim 1, wherein the resistance of said label resistor corresponds to the sensitivity of the second pump current to variations in the concentration of NOx contained in the measurement gas.

3. A connector for an NOx sensor according to claim 2, wherein the resistance of said label resistor corresponds to the first pump current as measured when the oxygen concentration of the measurement gas is identical to that of the atmosphere.

4. A connector for an NOx sensor according to claim 1, wherein the resistance of said label resistor corresponds to the first pump current as measured when the oxygen concentration of the measurement gas is identical to that of the atmosphere.

5. An NOx sensor for measuring the concentration of oxygen and NOx in a measurement gas containing oxygen and NOx, comprising a sensor body having at least two oxygen-pumping cells that pump oxygen to output first and second electric current signals, and a connector having terminals for transferring the electric current signals to an electronic control unit for determining the concentration of NOx in the measurement gas, wherein said NOx sensor includes a label component, said label component having a single electrical value which is input to the electronic control unit and combined with said first and second electric current signals, and said electrical value corresponding to both (i) a relationship between oxygen concentration of the measurement gas and current detected by one of the oxygen-pumping cells, and (ii) a relationship between NOx concentration of the measurement gas and current detected by the other oxygen-pumping cell.

6. An NOx sensor as claimed in claim 5, wherein said label component comprises a label resistor having a predetermined resistance corresponding to at least two characteristics of the NOx sensor body.

7. An NOx sensor as claimed in claim 6, wherein said label resistor comprises two terminals connected to opposing ends of the label resistor, said label resistor terminals being arranged in the connector parallel to the terminals transferring the electric current signals of said first and second oxygen-pumping cells.

8. An NOx sensor as claimed in claim 6, wherein the resistance value of the label resistor corresponds to a correction coefficient for determining NOx concentration.

9. An NOx sensor as claimed in claim 6, wherein the resistance value of the label resistor corresponds to both a first correction coefficient for determining oxygen concentration and to a second correction coefficient for determining NOx concentration.

10. An NOx sensor as claimed in claim 5, wherein said electrical value corresponds to a correction coefficient for calculating NOx concentration based on the current detected by one of the oxygen-pumping cells.

11. An NOx sensor as claimed in claim 10, wherein said label component comprises a label resistor comprising two terminals connected to opposing ends of the label resistor, said label resistor terminals being arranged in the connector parallel to the terminals transferring the electric current signals of said first and second oxygen-pumping cells.

12. An NOx sensor as claimed in claim 5, wherein said electrical value corresponds to both a first correction coefficient for calculating oxygen concentration based on the current detected by one of the oxygen-pumping cells and to a second correction coefficient for calculating NOx concentration based on the current detected by the other oxygen-pumping cell.

13. An NOx sensor comprising a sensor body and a connector for the sensor body, said NOx sensor detecting the concentration of oxygen and NOx contained in a measurement gas, said connector being connected to the sensor body and having input and output terminals for inputting and outputting signals to and from the sensor body, wherein the sensor body comprises a first measurement chamber having a first oxygen-pumping cell and an oxygen-concentration-measuring cell and communicating with measurement gas via a first diffusion-controlling layer, the first oxygen-pumping cell and the oxygen-concentration-measuring cell being each formed of an oxygen-ion conductive solid electrolyte layer sandwiched between porous electrodes; and a second measurement chamber having a second oxygen-pumping cell and communicating with the first measurement chamber via a second diffusion-controlling layer, the second oxygen-pumping cell being formed of an oxygen-ion conductive solid electrolyte layer sandwiched between porous electrodes, and wherein a first pump current is caused to flow to the first oxygen-pumping cell such that an output voltage from the oxygen-concentration-measuring cell is maintained at a constant value so as to control the concentration of oxygen contained in the first measurement chamber to a constant level; a constant voltage is applied to the second oxygen-pumping cell in such a direction that oxygen is pumped out from the second measurement chamber; and a second pump current that flows through the second oxygen-pumping cell as a result of the application of the constant voltage and according to the concentration of NOx contained in the measurement gas is detected, said connector further comprising:
a single label resistor having a resistance value defining first and second correction coefficients for calculating the concentration of oxygen contained in the measurement gas based on the first pump current and the concentration of NOx contained in the measurement gas based on the second pump current, respectively; and
a pair of label signal output terminals connected to opposite ends of said label resistor.

14. An NOx sensor for measuring the concentration of oxygen and NOx in a measurement gas containing oxygen and NOx, comprising a sensor body having at least two oxygen-pumping cells that pump oxygen to output first and second current signals, and a connector having terminals for transferring the current signals to an electronic control unit for determining the concentration of oxygen and NOx in the measurement gas, wherein said NOx sensor includes a label component, said label component having a single electrical value which is input to the electronic control unit and combined with said first and second current signals, and said electrical value defining first and second correction coefficients for calculating the concentration of oxygen contained in the measurement gas based on the current detected by one of the oxygen-pumping cells and the concentration of NOx contained in the measurement gas based on the current detected by the other oxygen-pumping cell.

15. An NOx sensor as claimed in claim 14, wherein said label component comprises a resistor having a single resistance value, said resistance value defining first and second correction coefficients for calculating the concentration of oxygen contained in the measurement gas based on the current detected by one of the oxygen-pumping cells and the concentration of NOx contained in the measurement gas based on the current detected by the other oxygen-pumping cell.

* * * * *